US00PP26988P3

(12) United States Plant Patent
Ilsink

(10) Patent No.: US PP26,988 P3
(45) Date of Patent: Aug. 2, 2016

(54) ***ROSA* PLANT NAMED 'INTROS03'**

(50) Latin Name: ***Rosa* hybrid**
Varietal Denomination: IntRos03

(71) Applicant: Robert Ilsink, Leersum (NL)

(72) Inventor: Robert Ilsink, Leersum (NL)

(73) Assignee: Interplant Roses B.V. (NL)

( * ) Notice: Subject to any disclaimer, the term of this patent is extended or adjusted under 35 U.S.C. 154(b) by 55 days.

(21) Appl. No.: 14/120,791

(22) Filed: Jun. 27, 2014

(65) Prior Publication Data

US 2015/0382524 P1 Dec. 31, 2015

(51) Int. Cl.
*A01H 5/02* (2006.01)

(52) U.S. Cl.
USPC ..... Plt./102

(58) Field of Classification Search
USPC ..... Plt./102
CPC ..... A01H 5/0222; A01H 5/0216
See application file for complete search history.

*Primary Examiner* — Kent L Bell
(74) *Attorney, Agent, or Firm* — Cassandra Bright

(57) ABSTRACT

A new and distinct *Rosa* cultivar named 'IntRos03' is disclosed, characterized by abundant flowering, compact form and unique flower coloration of bright red-purple with a darker red-purple eye. The new variety is a *Rosa*, normally produced as an outdoor garden or container plant.

2 Drawing Sheets

Latin name of the genus and species: *Rosa* hybrid.
Variety denomination: 'IntRos03'.

BACKGROUND OF THE INVENTION

The new *Rosa* cultivar is a product of a planned breeding program conducted by the inventor, Robert Ilsink, in Leersum, Netherlands. The objective of the breeding program was to produce new *Rosa* varieties for ornamental commercial applications. The cross resulting in this new variety was made during April of 2006.

The seed parent is the unpatented, proprietary variety referred to as *Rosa* 'B274-02'. The pollen parent is the commercial variety referred to as *Rosa* 'INTERBYLONERI'. The new variety was discovered in April of 2007 by the inventor in a group of seedlings resulting from the 2006 crossing, in a research greenhouse in Leersum, Netherlands.

Asexual reproduction of the new cultivar was performed by vegetative cuttings. This was first performed at a research greenhouse in Leersum, Netherlands in Summer of 2008 and has shown that the unique features of this cultivar are stable and reproduced true to type in more than 6 successive generations.

SUMMARY OF THE INVENTION

The cultivar 'IntRos03' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IntRos03' These characteristics in combination distinguish 'IntRos03' as a new and distinct *Rosa* cultivar:

1. Dark red-purple spot in center of flower.
2. Compact size.
3. Abundant flowering.
4. Bright red-purple petal color.

Plants of the new cultivar 'IntRos03' are similar to plants of the seed parent, *Rosa* 'B274-02' in most horticultural characteristics, however, plants of the new cultivar 'IntRos03' differs in the following:

1. Red-Purple flower color. The seed parent has a soft yellow colored flower, fading to white.
2. Approximately 5 to 10 petals per flower. The seed parent has approximately 25 petals per flower.

Plants of the new cultivar 'IntRos03' are similar to plants of the pollen parent; *Rosa* 'INTERBYLONERI' in most horticultural characteristics, however, plants of the new cultivar 'IntRos03' differs in the following;

1. Red-Purple flower color. The pollen parent has a pink and white colored flower.

COMMERCIAL COMPARISON

Plants of the new cultivar 'IntRos03' can also be compared to the commercial variety *Rosa* 'Interbyloneri', unpatented. These varieties are similar in most horticultural characteristics; however 'IntRos03' differs in the following:

1. Red-Purple flower color. Comparator has pink flower color that fades to white.
2. Less flower petals than this comparator variety.

BRIEF DESCRIPTION OF THE PHOTOGRAPHS

Figure 1:
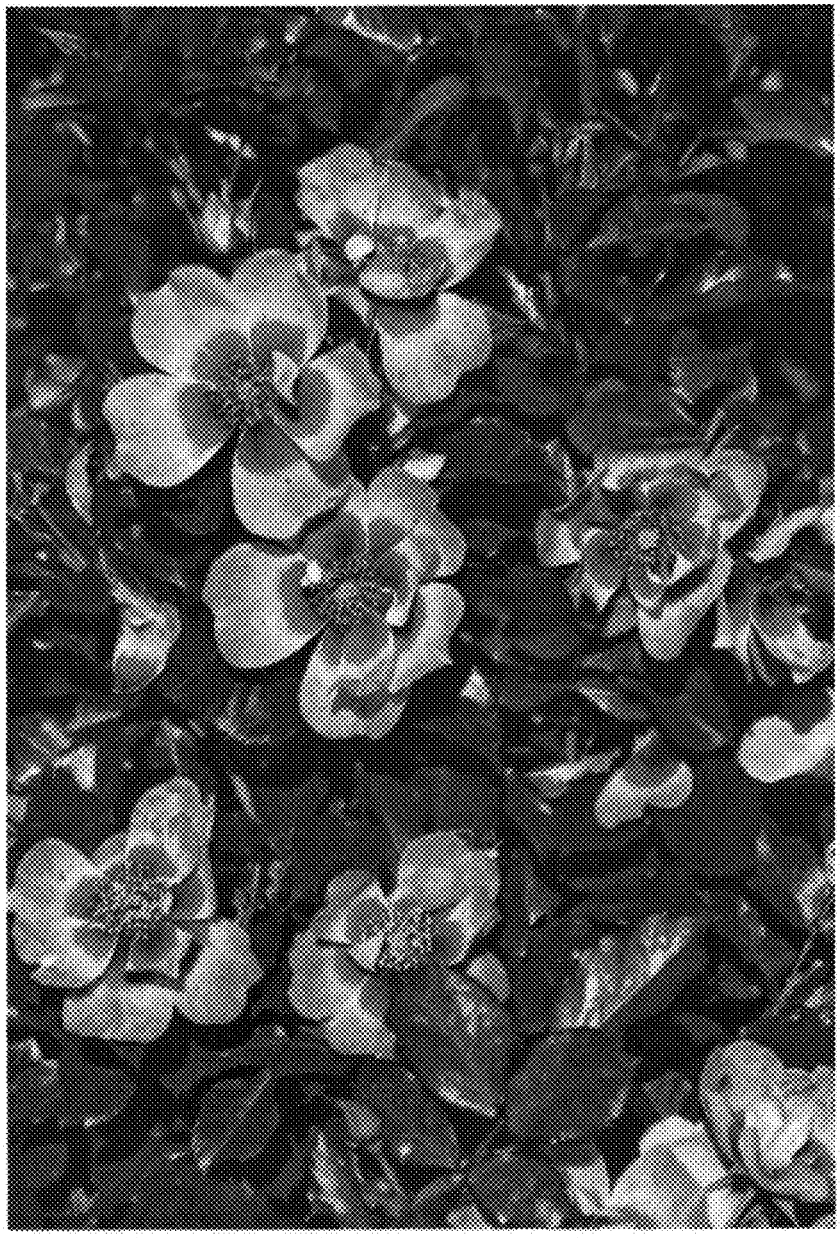

The accompanying photograph in FIG. 1 illustrates in full color a close up of multiple flowers, in various stages of maturity.

Figure 2:
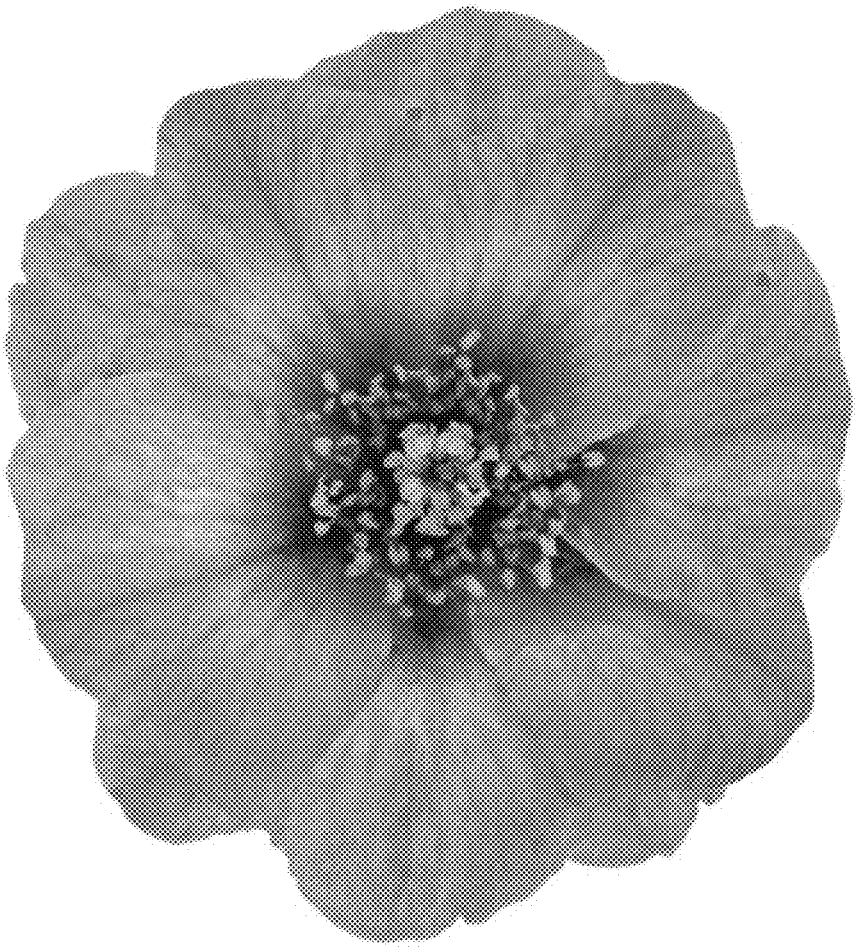

FIG. 2 illustrates a close up of a single mature flower.

The photographs were taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2001 except where general terms of ordinary dictionary significance are used. The following observations and measurements describe 'IntRos03' plants grown outdoors, in Leersum, Netherlands. The growing temperature ranged from approximately 0° C. to 28° C. during the day and from approximately −5° C. to 18° C. during the night. General light conditions are bright, normal sunlight. Measurements and numerical values represent averages of typical plant types.

Botanical classification: *Rosa* 'IntRos03'.

PROPAGATION

Time to initiate roots: About 15 days at approximately 20° C.

Time to produce a rooted cutting: About 35 days at approximately 20° C.

PLANT

Age of plant described: Approximately 2 years.
Growth habit: Compact spreading.
In a container or in the ground: In container.
Height: 500 mm (50 cm).
Plant spread: 500 mm (50 cm).
Rootstock: Own root.
Growth rate: Approximately 2 years to reach 0.5 meters.
Branching characteristics: Sympodial branching.
Length of primary lateral branches: Approximately 50 cm.
Diameter of lateral branches: Approximately 1 cm.
Quantity of lateral branches: Numerous.
Branching arrangement: Branching from every axillary bud possible.

Branches—young wood:
- *Diameter*.—Approximately 0.5 cm.
- *Texture*.—Herbaceous; glossy with anthocyanin coloration.
- *Approximately density/quantity of thorns*.—Highly variable, from sparse to moderately dense. No typical pattern of density observed.
- *Color*.—Near Purple RHS 79A.

Branches—old wood:
- *Diameter*.—Approximately 1 cm, after 2 years.
- *Color*.—Near Green RHS 141B.
- *Texture*.—Woody; semi glossy.

Thorns:
- *Approximately density/quantity of thorns*.—Highly variable, from sparse to moderately dense. No typical pattern of density observed.
- *Color of thorns*.—Immature: Red purple, closest to Red-Purple 60A. Mature: Near Greyed-Orange 166D, during Winter months.
- *Shape*.—Deltoid.
- *Height*.—Average range 0.6 cm to 1.3 cm.
- *Diameter*.—Base near 0.4 to 0.9 cm. Tip near 0.2 cm.

FOLIAGE

Leaf:
- *Arrangement*.—Alternate and compound.
- *Quantity*.—Approximately 6 per main branch.
- *Average length*.—Approximately 12 cm.
- *Average width*.—Approximately 8 cm.

Rachis:
- *Average length*.—Approximately 6.2 cm.
- *Average diameter*.—Approximately 0.3 cm.
- *Color*.—Near RHS Green 138C, in warmer months some flushing of Greyed-Red 178B.

Leaflet:
- *Quantity*.—Approximately 5 per leaf.
- *Average length*.—Approximately 4 cm.
- *Average width*.—Approximately 2.5 cm.
- *Shape of blade*.—Oval.
- *Apex*.—Pointed.
- *Base*.—Rounded.
- *Margin*.—Serrated.
- *Texture of top surface*.—Semi glossy.
- *Texture of bottom surface*.—Matte.
- *Appearance of top surface*.—Semi glossy.
- *Appearance of bottom surface*.—Matte.
- *Texture of top surface*.—Non-pubescent.
- *Texture of bottom surface*.—Non-pubescent.
- *Leaf internode length*.—4 cm.
- *Color*.—Young foliage upper side: Near Green RHS 133B. Young foliage under side: Near Green RHS 133B. Mature foliage upper side: Near Green RHS 126A. Mature foliage under side: Near Green RHS 126A.
- *Venation*.—Type: Reticulate. Venation color upper side: Indistinguishable from leaf blade. Venation color under side: Indistinguishable from leaf blade.

Petiole:
- *Average length*.—Approximately 4.0 cm.
- *Average diameter*.—Approximately 0.3 cm.
- *Color*.—Near RHS Green 138C, in warmer months some flushing of Greyed-Red 178B.
- *Texture*.—Glabrous, occasional irregularly occurring minute spine.

FLOWER

Natural flowering season: Spring until Autumn.
Begins flowering after how many years/months: 2 months.
Inflorescence type and habit: Raceme.
Rate of flower opening: Approximately 1 day from bud to fully opened flower.
Flower longevity on plant: 4 days, after fully opened.
Quantity of flowers: 3-5.

Inflorescence size:
- *Diameter*.—Approximately 15 cm.
- *Length*.—Approximately 15 cm.

Peduncle:
- *Length*.—3 cm.
- *Diameter*.—0.2 cm.
- *Color*.—Near RHS Green 138B, flushed Greyed-Purple 185B.

Petals:
- *Petal arrangement*.—Rotate overlapping.
- *Size*.—Medium.
- *Length*.—2.5 cm.
- *Width*.—2 cm.
- *Shape*.—Broad ovate.
- *Margin*.—Very shallowly notched or lobed, reflexed back and undulating.
- *Apex*.—Very shallowly notched or lobed.
- *Base*.—Obtuse.
- *Petal quantity*.—5.
- *Texture*.—Medium strong.

Color:
- *Petals*.—When opening: Upper surface: Near Red-Purple RHS 63A, base near Red-Purple 71A. Lower surface: Near Purple-Violet RHS 82B. Fully opened: Upper surface: Near Red-Purple RHS 63A. base near Red-Purple 59B, center halo near Red-Purple 69C. Lower surface: Near Purple-Violet RHS 82B. Color Changes when aging: Changing to Near Red-Purple RHS 69D.

Bud:
*Shape*.—Round.
*Length*.—Approximately 1.5 cm.
*Diameter*.—Approximately 1 cm.
*Color*.—Near Red-Purple RHS 63A and 63B, base near Red-Purple 69C.

Sepals:
*Length*.—1 cm.
*Width*.—0.4 cm.
*Shape*.—Narrow deltoid.
*Apex*.—Acuminate.
*Margin*.—Serrate.
*Color*.—Interior Surface: Near Green RHS 136A. Exterior Surface: Near Green RHS 136A.
*Texture*.—Non-pubescent, matte.

Receptacle:
*Length*.—0.7 cm.
*Width*.—0.7 cm.
*Shape*.—Flattened dome.
*Color*.—Near RHS Green 138D.

Fragrance: None.

REPRODUCTIVE ORGANS

Stamens:
*Quantity*.—Average range 70 to 110.
*Filament length*.—Approximately 0.8 cm.
*Filament color*.—Near Yellow RHS 6A.

Anthers:
*Length*.—0.2 cm.
*Shape*.—Linear.
*Color*.—Near Red-Purple RHS 63D.
*Pollen*.—Color: White 155D. Quantity: Many.

Pistil:
*Number*.—Approximately 60.
*Pistil length*.—Approximately 1.0 cm.
*Style*.—Length: Approximately 0.2 cm. Color Near Greyed-Green RHS 192A.
*Stigma*.—Shape: Linear. Color: Near Greyed-Green RHS 192A.
*Ovary color*.—Near RHS Yellow-Green 145C.

OTHER CHARACTERISTICS

Seeds and fruits: Not observed to date.

Disease/pest resistance: Good overall disease resistance to normal pests and diseases typical of garden roses.

What is claimed is:

1. A new and distinct cultivar of *Rosa* plant named 'IntRos03' as herein illustrated and described.

* * * * *